US00PP17166P2

(12) United States Plant Patent
Vanderhaegen

(10) Patent No.: US PP17,166 P2
(45) Date of Patent: Oct. 24, 2006

(54) ***RHODODENDRON* PLANT NAMED 'CHRISTINE BELLI'**

(50) Latin Name: *Rhododendron simsii*
Varietal Denomination: Christine Belli

(75) Inventor: Johan Vanderhaegen, Kruishoutem (BE)

(73) Assignee: Hortibreed NV, Lochristi (BE)

( * ) Notice: Subject to any disclaimer, the term of this patent is extended or adjusted under 35 U.S.C. 154(b) by 80 days.

(21) Appl. No.: 10/998,118

(22) Filed: Nov. 26, 2004

(51) Int. Cl.
*A01H 5/00* (2006.01)

(52) U.S. Cl. ..... Plt./238
(58) Field of Classification Search ..... Plt./238, Plt./239, 240
See application file for complete search history.

*Primary Examiner*—Kent Bell
(74) *Attorney, Agent, or Firm*—Mark P. Bourgeois

(57) ABSTRACT

A new cultivar of *Rhododendron* plant named 'Christine Belli' that is characterized by dark shiny green leaves, large white flowers with a slight greenish base and vigorous growth.

1 Drawing Sheet

Botanical classification: *Rhododendron simsii.*
Variety denomination: 'Christine Belli'.

BACKGROUND OF THE INVENTION

The present invention relates to a new and distinct cultivar of *Rhododendron* plant botanically known as *Rhododendron simsii* and hereinafter referred to by the cultivar name 'Christine Belli'.

'Christine Belli' was discovered as a naturally occurring branch mutation of the parent plant *Rhododendron* 'Christine Magic' (U.S. Plant Pat. No. 15,096). 'Christine Belli' was discovered in March of 2000 in a cultivated area of Moerbeke, Belgium.

Asexual reproduction of the new cultivar 'Christine Belli' by cuttings was first performed in October of 2000 in Moerbeke, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Rhododendron* cultivar 'Christine Belli'. These traits in combination distinguish 'Christine Belli' as a new and distinct cultivar apart from all other existing varieties of *Rhododendron* known to the inventor.

1. *Rhododendron* 'Christine Belli' exhibits dark shiny green leaves.
2. *Rhododendron* 'Christine Belli' exhibits white flowers with a slight greenish base.
3. *Rhododendron* 'Christine Belli' exhibits vigorous growth.
4. *Rhododendron* 'Christine Belli' exhibits large flowers.

The new cultivar 'Christine Belli' is distinguishable from the parent *Rhododendron* 'Christine Magic' by the following characteristics:

1. 'Christine Belli' has white flowers. The flowers of 'Christine Magic' are red.

The closest comparison cultivar is 'Christine Siena' (U.S. Plant Pat. No. 16,273). 'Christine Belli' is distinguishable from 'Christine Siena' by the following characteristics:

1. 'Christine Belli' has white flowers. The flowers of 'Christine Siena' are red.

BRIEF DESCRIPTION OF THE DRAWING

The accompanying photograph illustrates the distinguishing traits of *Rhododendron* 'Christine Belli'. The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Rhododendron* cultivar named 'Christine Belli'. Data was collected in Kruishoutem, Belgium from 24 month old greenhouse grown plants in 1.0 liter containers. The time of year was Fall and the average temperature was 20° Centigrade during the Summer and 4° Centigrade during the Winter. The light level was natural outdoor light and there were no photoperiodic treatments. OSMOCOTE and NPK were applied. Color determinations are in accordance with The Royal Horticultural Society Colour Chart 2001 edition, except where general color terms of ordinary dictionary significance are used. The growing requirements are similar to the species. 'Christine Belli' has not been tested under all possible conditions and phenotypic differences may be observed with variations in environmental, climatic, and cultural conditions, however, without any variance in genotype.

Botanical classification: *Rhododendron* 'Christine Belli'.
Use: Ornamental Perennial Shrub.
Parentage: 'Christine Belli' is a naturally occurring branch mutation of *Rhododendron simsii* 'Christine Magic'.
Vigor: Moderate.
Growth rate: Approximately 8 cm. in height and 15 cm. in width per year.

Growth habit: Broad Upright, densely branched.
Plant shape: Flattened globose.
Suitable container size: 1.0 liter container.
Height: Average 17 cm. in height.
Width: Average 33 cm. in width.
Hardiness: USDA Zone 9.
Propagation: Cuttings.
Time to initiate roots: Approximately 30 days to produce roots on an initial cutting.
Time to produce a rooted cutting or liner: Approximately 60 days.
Root system: Fine and fibrous.
Stem:
*Branching habit.*—Freely branching.
*Average number of lateral branches.*—6.
*Pinching.*—Yes.
*Lateral branch diameter.*—3 cm. in diameter.
*Lateral branch length.*—11 cm. in length.
*Lateral branch strength.*—Moderately strong.
*Stem color.*—144B, older stems 200C to 200D.
*Pubescence.*—Dense, length 1.5 mm, color 175C to 175D.
*Internode length.*—8 mm. between nodes.
*Shape.*—Round.
*Surface.*—Dull.
*Stem strength.*—Moderately strong.
Foliage:
*Texture.*—Glossy, slightly leathery.
*Leaf arrangement.*—Alternate, clustered towards the top of the stems.
*Compound or single.*—Single.
*Quantity of leaves per lateral branch.*—22.
*Leaf shape.*—Elliptic to obovate.
*Leaf apex.*—Mucronulate.
*Leaf base.*—Attenuate.
*Leaf length.*—3.8 cm. in length.
*Leaf width.*—1.8 cm. in width.
*Pubescence.*—Slight, both sides, length 1 mm, color grey-orange 175C to 175D.
*Leaf margin.*—Entire.
*Vein pattern.*—Pinnate.
*Young leaf color* (*upper surface*).—Between 141A and 143A.
*Young leaf color* (*lower surface*).—138A to 138B.
*Mature leaf color* (*upper surface*).—Between 139A and 189A.
*Mature leaf color* (*lower surface*).—137B.
*Vein color* (*lower surface*).—143C.
*Vein color* (*upper surface*).—143A.
*Leaf attachment.*—Petiolate.
*Petiole dimensions.*—6 mm in length, slightly flattened 2 mm. in width, 1 mm in height.
*Petiole color.*—143C.
*Durability of foliage to stress.*—Moderate.
Flower:
*Flower arrangement.*—Terminal clusters.
*Inflorescence type.*—Semi-double.
*Inflorescence dimensions.*—10.4 cm. in diameter and 5.5 cm. in height.
*Flowering habit.*—Continuously once a year.
*Quantity of flowers per lateral stem.*—Approximately 5.
*Quantity of flower buds per lateral stem.*—Approximately 5.
*Quantity of flowers and buds per plant.*—Approximately 60.
*Flowering season.*—Late winter to early summer.
*Time to flower or response time.*—10 months.
*Rate of flower opening.*—After the first flower of a cluster has opened, all flowers of that cluster will open in approximately 14 days.
*Fragrance.*—None.
*Self-cleaning or persistent.*—Self-cleaning.
*Flower bud length.*—9 mm. in length.
*Flower bud diameter.*—7 mm. in diameter.
*Flower bud shape.*—Ovate.
*Bud color.*—157A to 157D.
*Rate of bud opening.*—10 days.
*Flower aspect.*—Upright to outward.
*Flower shape.*—Funnelform.
*Flower dimensions.*—5.4 cm. in diameter and 3.4 cm. in height.
*Flower longevity.*—Lasts approximately 24 days on plant.
*Petal appearance.*—Dull, slight velvety.
*Petal texture.*—Glabrous.
*Petal arrangement.*—Funnelform, petals placed rotate.
*Number of petals.*—Five in number.
*Petals fused or unfused.*—Lower 33% fused.
*Petal shape.*—Irregular obovate.
*Petal margin.*—Entire, slightly wavy.
*Petal apex.*—Rounded to praemorse.
*Petal dimensions.*—3.8 cm. in length and 1.9 cm. in width.
*Petal color when opening* (*upper side*).—155A with a base 157D.
*Petal color when opening* (*under side*).—155A, with a base irregularly dotted 145A to 145B.
*Petal color when fully opened* (*upper side*).—N155A with a base 157D.
*Petal color when fully opened* (*under side*).—N155A, with a base irregularly dotted 145A to 145B.
*Petal color fading to.*—Not fading.
*Petaloid appearance.*—Dull, slightly velvety.
*Petaloid arrangement.*—Rotate, in the center of the flower.
*Petaloid number.*—5 in number.
*Petaloid shape.*—Irregular, obovate to narrow obovate.
*Petaloid margin.*—Entire.
*Petaloid dimensions.*—3.6 cm. in length and 1.8 cm. in width.
*Petaloid color immature.*—N155A with a base irregularly dotted 145Ato 145B.
*Petaloid color mature.*—N155A with a base irregularly dotted 145A to 145B.
Calyx:
*Calyx shape.*—Campanulate.
*Calyx dimensions.*—7 mm. in length and 1.1 cm. in diameter.
Sepals:
*Sepal appearance.*—Dull, pubescent.
*Sepal arrangement.*—Campanulate.
*Number of sepals.*—Five in number.
*Sepals fused or unfused.*—Lower 25% fused.
*Sepal shape.*—Ovate.
*Sepal margin.*—Entire.
*Sepal apex.*—Acute.
*Sepal base.*—Fused into campanulate calyx.
*Sepal dimensions.*—7 mm. in length and 4 mm. in width.
*Sepal color when opening* (*upper side*).—143B.
*Sepal color when opening* (*under side*).—138B.

*Sepal color mature* (*upper side*).—143B.
*Sepal color mature* (*under side*).—138B.

Bracts:
*Number of bracts.*—5 in number.
*Bract dimensions.*—1.2 cm. in length and 7 mm. in width.
*Bract shape.*—Ovate.
*Bract apex.*—Acute.
*Bract pubescence.*—Sparse on under side, length 1.5 mm, color 175C to 175D.
*Bract color* (*both sides*).—144A to 144B.

Pedicels:
*Pedicel dimensions.*—1.2 cm. in length and 2 mm. in diameter.
*Pedicel angle.*—75° from horizontal.
*Pedicel color.*—138A to 138B.
*Pedicel strength.*—Moderate.

Reproduction organs:
*Stamen number.*—1.
*Anther shape.*—Dorsifixed, oval, usually not fully developed.
*Anther dimensions.*—2 mm in length.
*Anther color.*—163A.
*Filament length.*—1.2 cm.
*Filament color.*—N155A.
*Amount of pollen.*—Very low.
*Pistil number.*—1 in number.
*Pistil dimensions.*—1.8 cm. in length.
*Stigma shape.*—Club shaped, flattened at the top.
*Stigma color.*—144B.
*Style length.*—1.75 mm.
*Style color.*—145C with a base 145A.
*Ovary color.*—138A to 138B.

Seed: Seed production has not been observed.

Disease and pest resistance: Plants of the new *Rhododendron* have not been observed for disease or pest resistance.

It is claimed:

1. A new and distinct variety of *Rhododendron* plant named 'Christine Belli' as described and illustrated.

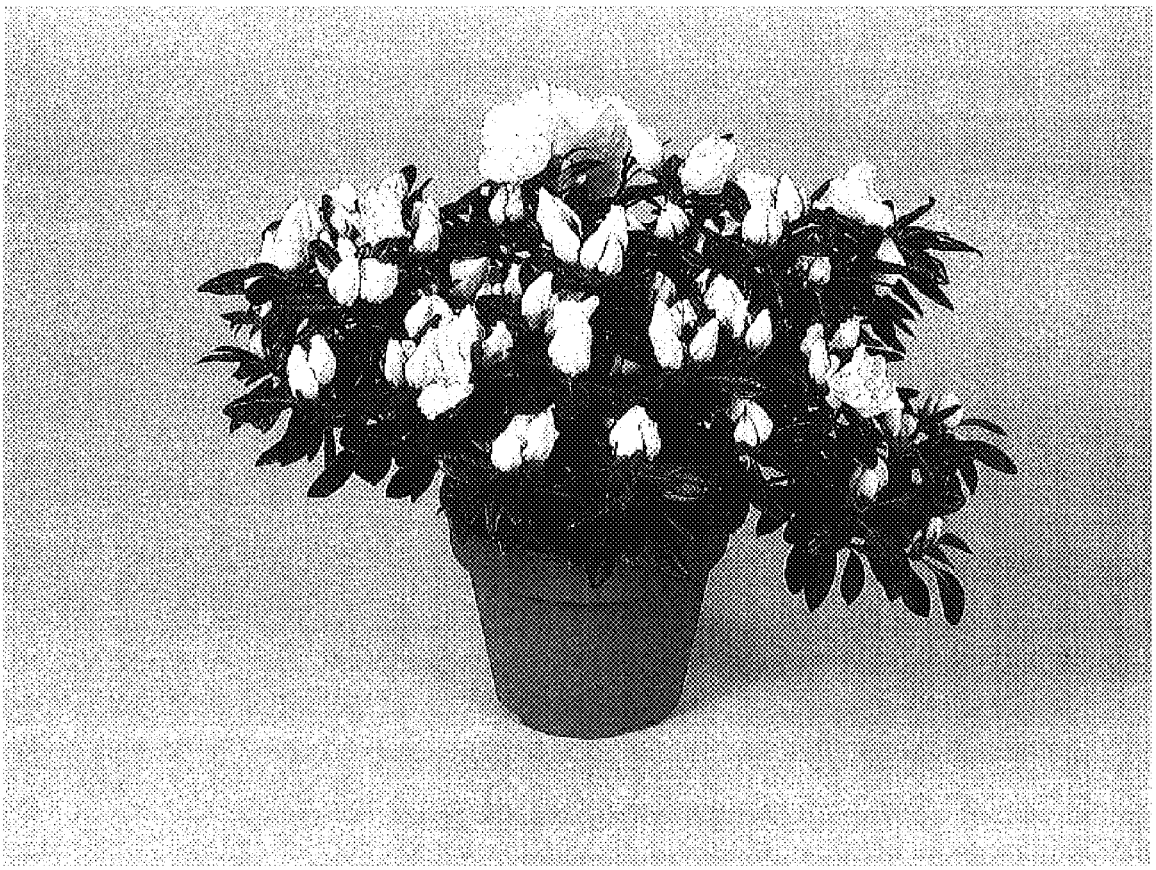

* * * * *